United States Patent [19]

Nishiyama et al.

[11] 4,367,336

[45] Jan. 4, 1983

[54] 2-SUBSTITUTED-5-TRIFLUOROMETHYL-PYRIDINES AND PROCESS FOR PRODUCING THE SAME

[75] Inventors: Ryuzo Nishiyama, Takatsuki; Kanichi Fujikawa; Isao Yokomichi, both of Moriyama; Takahiro Haga, Kusatsu; Toru Koyanagi, Kyoto, all of Japan

[73] Assignee: Ishihara Sangyo Kaisha, Ltd., Osaka, Japan

[21] Appl. No.: 237,056

[22] Filed: Feb. 23, 1981

[30] Foreign Application Priority Data

Feb. 21, 1980 [JP] Japan .................................. 55-21221
Feb. 21, 1980 [JP] Japan .................................. 55-21222

[51] Int. Cl.³ ................... C07D 213/84; C07D 213/55
[52] U.S. Cl. ..................................... 546/286; 546/326
[58] Field of Search ................................ 546/286, 326

[56] References Cited

U.S. PATENT DOCUMENTS

| 3,271,441 | 9/1966 | Brace | 546/286 |
| 3,914,239 | 10/1975 | Kühnis et al. | 546/326 |
| 4,184,041 | 1/1980 | Nishiyama et al. | 546/345 |

FOREIGN PATENT DOCUMENTS

| 2305758 | 8/1973 | Fed. Rep. of Germany | 546/320 |
| 2307444 | 8/1974 | Fed. Rep. of Germany | 546/286 |
| 2079649 | 11/1971 | France | 546/286 |

OTHER PUBLICATIONS

Kobayashi et al., Chem. Pharm. Bull. 17(3), pp. 510–514, (1969).
Chem. Abstracts, 66:85737f.

*Primary Examiner*—Ethel G. Love
*Attorney, Agent, or Firm*—Sughrue, Mion, Zinn, Macpeak and Seas

[57] ABSTRACT

A 2-substituted-5-trifluoromethylpyridine compound represented by Formula (I):

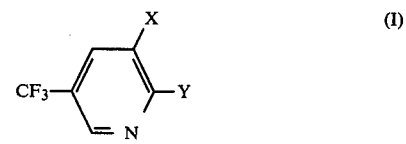

wherein X is a hydrogen atom or a halogen atom, and Y is a cyano group or a carboxy group, provided that Y is a cyano group, then X is a halogen atom, or a salt thereof, and a process for the production of the same. This compound is useful as an intermediate for the production of various fine chemicals.

2 Claims, No Drawings

2-SUBSTITUTED-5-TRIFLUOROMETHYLPYRIDINES AND PROCESS FOR PRODUCING THE SAME

FIELD OF THE INVENTION

This invention relates to a 5-trifluoromethylpyridine having a substituent at the 2-position thereof (hereinafter, referred to as "a 2-substituted-5-trifluoromethylpyridine"), which is useful as an intermediate for the production of various fine chemicals, such as an insecticide, and a process for producing the same.

BACKGROUND OF THE INVENTION

A 2-substituted-5-trifluoromethylpyridine of this invention is a novel compound and no disclosure concerning this compound can be found in any literature although 2-cyano-5-trifluoromethylpyridine similar to said compound is described in Chemical Pharmaceutical Bulletin, Vol. 17, No. 3, pages 510 to 514 (1969).

SUMMARY OF THE INVENTION

An object of this invention is to provide a novel 2-substituted-5-trifluoromethylpyridine compound which is useful as an intermediate for the production of various chemicals, such as an insecticide.

Another object of this invention is to provide a process for the production of a 2-substituted-5-trifluoromethylpyridine compound with advantage on an industrial scale.

The 2-substituted-5-trifluoromethylpyridine of this invention is a compound represented by Formula (I):

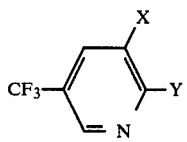

wherein X is a hydrogen atom or a halogen atom, and Y is a cyano group or a carboxy group, provided that when Y is a cyano group, then X is a halogen atom, or a salt thereof.

DETAILED DESCRIPTION OF THE INVENTION

This invention provides a compound represented by Formula (I):

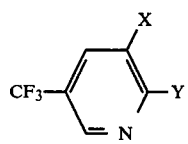

wherein X is a hydrogen atom or a halogen atom, and Y is a cyano group or a carboxy group, provided that when Y is a cyano group, then X is a halogen atom, or a salt thereof, and a process for the production of the same.

The halogen atom represented by X in Formula (I) indicates fluorine, chlorine, bromine, and iodine. By the term "salt" as herein used is meant a salt of 5-trifluoromethylpyridine-2-carboxylic acid (in Formula (I)), Y is a carboxy group) and an alkaline substance.

The 2-substituted-5-trifluoromethylpyridine compound of this invention can generally be prepared as follows:

Method (1): Preparation of 2-Cyano-3-halogeno-5-trifluoromethylpyridine of Formula (III):

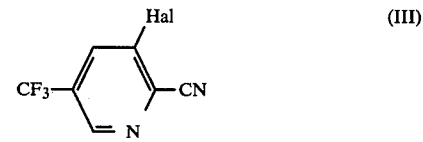

wherein Hal is a halogen atom, such as fluorine, chlorine, bromine and iodine.

Compound (III) can be prepared by cyanating a 2-bromo-3-halogeno-5-trifluoromethylpyridine represented by Formula (IV'):

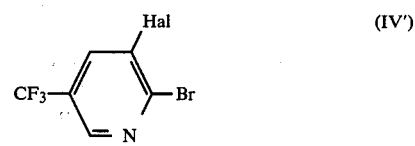

wherein Hal is the same as defined above, in the presence of a cyanating agent. Suitable cyanating agents which can be used include cuprous cyanide, potassium cyanide and so on. A suitable amount of the cyanating agent added is from 1.0 to 1.5 mols, preferably from 1.1 to 1.3 mols, per mol of the 2-bromo-3-halogeno-5-trifluoromethylpyridine.

The cyanation reaction is preferably carried out in an aprotic polar solvent, but it can be effected in the absence of any solvent. Suitable aprotic polar solvents which can be used include aromatic amines, e.g., pyridine, quinoline, etc., dimethylformamide, dimethyl sulfoxide, N-methylpyrrolidone, hexamethylphosphoric triamide and so on.

The reaction temperature is from 50° to 150° C., preferably from 100° to 130° C., and the reaction time is 1 hour or less, preferably from 10 to 30 minutes.

The starting material, 2-bromo-3-halogeno-5-trifluoromethylpyridine can be prepared, for example, by reacting a 2-chloro-3-halogeno-5-trifluoromethylpyridine, which is disclosed in European Patent Publication No. 0000483, with hydrogen bromide at 40° to 50° C.

Method (2): Preparation of 5-Trifluoromethylpyridine-2-carboxylic Acid of Formula (II) or Salt Thereof:

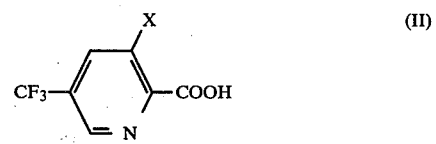

wherein X is the same as defined above.

Compound (II) or salt thereof can be prepared by the following Method (2-1) or (2-2):

Method (2-1) A 2-bromo-5-trifluoromethylpyridine represented by Formula (IV):

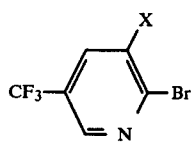

(IV)

wherein X is the same as defined above, is reacted with carbon dioxide in a solvent in the presence of an organometallic compound in an atmosphere of an inert gas, e.g., nitrogen, to prepare Compound (II) or salt thereof.

Suitable solvents which can be used include ethers, e.g., diethyl ether, tetrahydrofuran, dioxane, etc. Suitable organometallic compounds which can be used include organolithium compounds, e.g., butyl lithium, phenyl lithium, etc., organosodium compounds, e.g., phenyl sodium, etc., and so on. A suitable amount of the organometallic compound added is from 1.0 to 3.0 mols, preferably from 1.5 to 2.0 mols, per mol of the 2-bromo-5-trifluoromethylpyridine.

The reaction temperature is from $-50°$ to $-100°$ C., preferably from $-60°$ C. to $-80°$ C., and the reaction time is from 30 minutes to 2 hours, preferably from 45 minutes to 1.5 hours.

Method (2-2) A 2-cyano-5-trifluoromethylpyridine represented by Formula (III'):

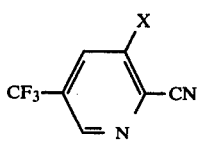

(III')

wherein X is the same as described above, which can be prepared by Method (1) above or an analogous method, is hydrolyzed in a solvent in the presence of an alkali metal hydroxide or a mineral acid to prepare Compound (II) or salt thereof.

Suitable solvents which can be used include water and alcohols, e.g., methanol, ethanol, ethylene glycol, etc. Suitable alkali metal hydroxides which can be used in the hydrolysis include sodium hydroxide, potassium hydroxide and so on, and suitable examples of mineral acids which can be used include hydrochloric acid, sulfuric acid and so on. A suitable amount of the alkali metal hydroxide or mineral acid used is from 1.0 to 2.0 mols, preferably from 1.1 to 1.5 mols, per mol of the 2-cyano-5-trifluoromethylpyridine.

The temperature at which the hydrolysis is performed is from 20° to 150° C., preferably from 60° to 100° C., and the reaction time is from 2 to 12 hours, preferably from 4 to 8 hours.

Typical examples of the 2-substituted-5-trifluoromethylpyridines of this invention are given below:

2-Cyano-3-halogeno-5-trifluoromethylpyridines

2-Cyano-3-chloro-5-trifluoromethylpyridine b.p.: 92° C./19 mmHg

2-Cyano-3-bromo-5-trifluoromethylpyridine b.p.: 108° C./15 mmHg

2-Cyano-3-fluoro-5-trifluoromethylpyridine b.p.: 93°–97° C./45 mmHg

2-Cyano-3-iodo-5-trifluoromethylpyridine

5-Trifluoromethylpyridine-2-carboxylic Acids

3-Chloro-5-trifluoromethylpyridine-2-carboxylic Acid m.p.: 88°–91° C.

3-Bromo-5-trifluoromethylpyridine-2-carboxylic Acid m.p.: 64°–68° C.

5-Trifluoromethylpyridine-2-carboxylic Acid m.p.: 129°–130° C.

3-Fluoro-5-trifluoromethylpyridine-2-carboxylic Acid

3-Iodo-5-trifluoromethylpyridine-2-carboxylic Acid

Sodium, potassium and amine salts can also be exemplified.

The following Preparation Examples are given to illustrate this invention in greater detail.

Preparation Example 1

Ten grams of 2-bromo-3-chloro-5-trifluoromethylpyridine was dissolved in 100 ml of dry diethyl ether in a nitrogen stream, and the resulting solution was cooled to $-78°$ C. To the solution thus cooled was gradually dropwise added 30 ml of a 15% solution of n-butyl lithium in hexane, and the resulting mixture was stirred at that temperature for 30 minutes. Thereafter, an excessive amount of pulverized dry ice was gradually introduced into the solution.

The temperature of the solution was returned to room temperature, and the solution was stirred at that temperature for an additional 1 hour. After the reaction was completed, 100 ml of water was added to thereby subject to the extraction. An aqueous layer thus formed was isolated and made acidic by adding thereto concentrated hydrochloric acid to form an oily product. The thus formed oily product was extracted with 300 ml of methylene chloride. After drying an organic layer over anhydrous sodium sulfate, the solvent was evaporated off under reduced pressure to obtain 5.1 g of 3-chloro-5-trifluoromethylpyridine-2-carboxylic acid.

Preparation Example 2

The same procedure as in Preparation Example 1 was repeated except that 10 g of 2-bromo-5-trifluoromethylpyridine was used in place of 2-bromo-3-chloro-5-trifluoromethylpyridine, to thereby obtain 5.8 g of 5-trifluoromethylpyridine-2-carboxylic acid.

Preparation Example 3

Forty one grams of 2-bromo-3-chloro-5-trifluoromethylpyridine was dissolved in 100 ml of dimethylformamide at room temperature, and after the addition of 17 g of cuprous cyanide thereto, the resulting solution was gradually heated to 120° C. After the solution was maintained at 120° C. for 10 minutes, the heating was stopped, and the solution was stirred for 30 minutes.

After the reaction was completed, the reaction solution was poured into 200 ml of ammonia water to decompose a copper complex, and 500 ml of diethyl ether was then added thereto to perform the extraction. The ethereal layer thus obtained was dried over anhydrous sodium sulfate. The solvent was evaporated off under reduced pressure, and the residue was distilled under reduced pressure to obtain 24 g of 2-cyano-3-chloro-5-trifluoromethylpyridine.

Preparation Example 4

The same procedure as in Preparation Example 3 was repeated except that 37 g of 2-bromo-3-fluoro-5-trifluoromethylpyridine was used in place of 2-bromo-3- chloro-5-trifluoromethylpyridine, to thereby obtain 17 g of 2-cyano-3-fluoro-5-trifluoromethylpyridine.

Preparation Example 5

Twenty four grams of 2-cyano-3-chloro-5-trifluoromethylpyridine was dissolved in 100 ml of ethanol, and 10 ml of an aqueous solution containing 5.6 g of sodium hydroxide was dropwise added to the resulting solution at room temperature. The reaction solution was heated to 80° C., and stirred under reflux conditions for 5 hours.

After the reaction was completed, the solvent was evaporated off under reduced pressure, and a mixture of 50 ml of diethyl ether and 200 ml of water was added to the residue to perform the extraction. An aqueous layer thus obtained was isolated and made acidic to a pH of 2 by adding thereto concentrated hydrochloric acid to form an oily product. The oily product thus obtained was extracted with 500 ml of methylene chloride. An organic layer thus obtained was dried over anhydrous sodium sulfate and, the solvent was evaporated off under reduced pressure to obtain 19 g of 3-chloro-5-trifluoromethylpyridine-2-carboxylic acid.

Preparation Example 6

The same procedure as in Preparation Example 5 was repeated except that 20 g of 2-cyano-5-trifluoromethylpyridine was used in place of 2-cyano-3-chloro-5-trifluoromethylpyridine, to obtain 15 g of 5-trifluoromethylpyridine-2-carboxylic acid.

The 2-substituted-5-trifluoromethylpyridine compound of this invention is useful as an intermediate for the production of various fine chemicals. In other words, the compound of this invention can, for example, be easily derived into an insecticidal or acaricidal compound which is effective in inhibiting and controlling various insects and acari harmful to crops in agriculture and horticulture.

For example, 3-chloro-5-trifluoromethylpyridine-2-carboxylic acid is reacted with thionyl chloride whereby 3-chloro-5-trifluoromethylpicolinoyl chloride can be obtained. This compound is reacted with O-methylhydroxyamine hydrochloride at room temperature for 4 hours in the presence of potassium carbonate to obtain N-methoxy-3-chloro-5-trifluoromethylpyridine-2-carboximidic acid which is then reacted with O,O-diethylthionophospholic acid diester chloride at 50° C. for 24 hours in the presence of potassium carbonate to thereby obtain O,O-diethyl-O-(N-methoxy-3-chloro-5-trifluoromethylpyridine-2-carboximidoyl)thionophosphate ($n_D^{16.0} = 1.5054$).

In the insecticidal testing of this compound in a concentration of 200 ppm against larvae of diamondback moth in 2nd or 3rd instar, a 100% insecticidal effect can be obtained.

While the invention has been described in detail and with reference to specific embodiments thereof, it will be apparent to one skilled in the art that various changes and modifications can be made therein without departing from the spirit and scope thereof.

What is claimed is:

1. 3-chloro-5-trifluoromethylpyridine-2-carboxylic acid.

2. 2-cyano-3-chloro-5-trifluoromethylpyridine.

* * * * *